United States Patent [19]
Johnson et al.

[11] 3,967,030
[45] June 29, 1976

[54] SILOXANES

[75] Inventors: Gordon Carlton Johnson, Armonk; Richard Bruce Metzler, Ossining, both of N.Y.; Donald Leroy Bailey, Sistersville, W. Va.

[73] Assignee: Union Carbide Corporation, New York, N.Y.

[22] Filed: Jan. 22, 1975

[21] Appl. No.: 543,127

Related U.S. Application Data

[62] Division of Ser. No. 390,408, Aug. 22, 1973.

[52] U.S. Cl. .............................. 428/266; 428/409; 428/447; 260/448.2 H
[51] Int. Cl.$^2$ .......................................... B32B 33/00
[58] Field of Search .......... 428/266, 447, 452, 543, 428/409, 321, 320; 260/448.2 H

[56] References Cited

UNITED STATES PATENTS

| | | | |
|---|---|---|---|
| 2,547,678 | 4/1951 | Wilcock | 260/448.2 R |
| 2,895,853 | 7/1959 | Bailey et al. | 427/391 |
| 3,334,122 | 8/1967 | Cekada et al. | 260/448.2 R |
| 3,434,875 | 3/1969 | Smith et al. | 428/266 |
| 3,649,349 | 3/1972 | Grenoble | 428/447 |
| 3,697,473 | 10/1972 | Polmanteer et al. | 260/448.2 D |
| 3,772,247 | 11/1973 | Flannigan | 260/448.2 H |

*Primary Examiner*—Marion E. McCamish
*Assistant Examiner*—William R. Dixon, Jr.
*Attorney, Agent, or Firm*—Francis M. Fazio

[57] ABSTRACT

Siloxane quadripolymers containing W, X, Y and Z groups, as herein defined, are applied to impart excellent water repellency to fabrics and papers.

5 Claims, No Drawings

SILOXANES

This application is a division of application Ser. No. 390,408, filed Aug. 22, 1973.

The prior art has disclosed many siloxane compositions that can be used to impart water repellency to fabrics. However, there is still a need for improvements, both from the economic point of view and in the properties of the treated fabrics.

While it is known to produce siloxane polymers containing different siloxy moieties, it has not yet been shown, to the best of our knowledge, that the quadripolymers herein defined have previously been produced. Nor has it been shown, to the best of our knowledge, that such quadripolymers are effective water repellents for the treatment of fabrics and paper.

The quadripolymers of this invention are those containing W, X, Y and Z units as hereinafter defined, in which the number of such units present in the molecule and the ratios of each to the other are of importance in obtaining good fabric treatment properties. Quadripolymers other than those having the indicated number of each unit and the ratios recited can also be produced if desired.

In this specification the siloxane units are represented by the letters W, X, Y, and Z in which,

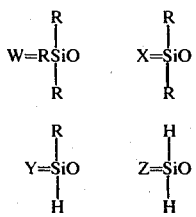

R is a lower alkyl group of from 1 to 3 carbon atoms, e.g., methyl, ethyl, propyl; preferably methyl. If desired R can contain more than 3 carbon atoms.

The siloxanes can be represented by the general formula $W X_a Y_b Z_c W$ in which $a$ has a value of from 27 to 55, $b$ has a value of from 4 to 15 and $c$ has a value of from 4.5 to 10. In these siloxanes the ratio of Y:X can vary from 0.1:1 to 0.35:1 and is preferably 0.15:1; the ratio of Z:X can vary from 0.1:1 to 0.25:1 and is preferably 0.17:1; 1; and the ratio of Y:Z can vary from about 0.9:1 to 1.6:1 and is preferably from 1.5:1 to 1.6:1. The degree of polymerization is preferably from 35 to 80, most preferably from 38 to 55. The term degree of polymerization means the total number of W, X, Y and Z units in the molecule. The siloxanes most preferred are those falling within the above definition having a kinematic viscosity below 100 cstks., preferably from 35 to 90 cstks. measured at 25°C., and can be as low as 20 cstks. However, also suitable are those siloxanes having a degree of polymerization up to 175 or more. These can be used but present some difficulties, on occasion, in preparation of suitable emulsions or dispersions due to their higher viscosities. As previously indicated quadripolymers can also be produced in which the values of $a$, $b$ and $c$ and the ratios thereof can be lesser or greater than those specifically set forth above, however, these do not possess the desired water repellency properties when applied to fabrics, papers, or other substrates.

The preparation of the quadripolymers can be carried out by any of the conventional procedures used in the production of siloxanes. These procedures are well known to the average chemist skilled in this art and do not require detailed description herein. A typical procedure is the so-called equilibration process, as exemplified by Examples 1 to 4 hereof. However, any other process can be used that will produce the quadripolymers.

The quadripolymers have the structure

These are to be distinguished over known copolymers and terpolymers of the structures

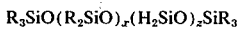

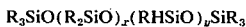

The substrates that can be treated by our quadripolymer siloxane compositions are the natural materials such as paper, cotton, wool, linen, etc., the synthetics such as acetate rayon, polyamides, polyesters, etc., or blends of any of these, all of which are well known.

The emulsions containing the siloxanes of this invention are produced by conventional means using the well known emulsifying and dispersing compounds. The emulsion or dispersion can contain mixtures of the quadripolymers siloxanes or they can comprise mixtures of one or more thereof with other known siloxane or other type of water repellent. A catalyst is normally present in order that the cure requirements correspond to the demands of commercial operations. In some instances it may be advisable to employ a solution of the siloxane. In preparing emulsions or dispersions any suitable nonionic, cationic or anionic emulsifier can be used. Illustrative thereof one can mention trimethylnonylpolyethylene glycol ether/nonylphenylpolyethylene glycol ether blends, poly(vinyl alcohol), polyoxyethylene esters of mixed fatty acids, N-cetylethyl morpholinium ethosulfate, cationic starch (either alone or in combination with poly(vinyl alcohol)), sodium lignin sulfonate, lauryl alcohol in combination with poly(vinyl alcohol), and the like. They are generally present at concentrations of from 1 to 15 weight per cent of the siloxane.

The quadripolymer siloxane composition, whether in emulsion or dispersion or solution, is applied to the substrate by any conventional procedure known in the art and then cured at 110°C. to 175°C. to meet the speed requirements for commercial operations. The loading ranges from about 0.2 per cent to 3 per cent or more by weight of the quadripolymer siloxane.

Among the catalysts normally used are the metal salts of strong acids, e.g., aluminum sulfate, zinc nitrate; metal soaps, e.g., zinc 2-ethylhexanoate, dibutyl tin diacetate, dibutyl tin dilaurate. The catalysts are generally present at a concentration of 0.1 to 10 weight per cent of the siloxane polymer with 2 per cent being typical. The metal soaps are generally preferred.

Among the other additives that can be present in conjunction with the quadripolymer siloxane in the treating bath one can mention starch, other water repellents, oil repellents, wash-wear resins, softeners and lubricants, dyes and pigments, anti-slip agents, and the like, provided they are compatible and do not interfere with and seriously diminish the water repellency properties of the quadripolymer siloxanes.

In addition to their use as water repellents, the siloxanes are good release agents when applied to paper substrates from compositions thereof.

The following examples serve to illustrate the invention. Parts are by weight unless otherwise indicated.

EXAMPLE 1

A mixture of 165 parts of $WX_{53}Z_9W$, 31.15 parts of $WY_{40}W$ and 3.86 parts of $WW$ were placed in a polymerization reactor equipped with a stirrer, thermometer and condenser. After thorough mixing one weight per cent of Amberlyst 15 (Rohm and Haas), a macroreticular sulfonic acid cationic exchange resin, was added as catalyst and the contents heated and stirred at 80°C. for 24 hours. The mixture was cooled to 30°C., decanted and sufficient sodium bicarbonate was added to neutralize the residual acidity and it was stirred for several hours before filtering. The siloxane produced had the average structure $WX_{26.8}Y_{6.7}Z_{4.5}W$. It had a kinematic viscosity of 88 cstks. at 25°C., a Y:X ratio of 0.25:1, a Z:X ratio of 0.17:1 and a Y:Z X ratio of 1.47:1.

An aqueous emulsion was prepared by adding 0.64 part of melted Tergitol NP-40 (Union Carbide) the reaction of 20 moles of ethylene oxide with nonylphenol to 0.96 part of Tergitol TMN (Union Carbide) the reaction product of 6 moles of ethylene oxide with trimethylnonanol. To this there was added 40 parts of the above siloxane and thoroughly mixed. To the mixture was added 58.2 parts of water having a pH of 3.3 to 3.8 and containing about 0.2 parts of a fungicide, while stirring vigorously. It was then passed through a homogenizer and, if required, the pH adjusted to the above range with dilute acid.

The emulsion was applied by conventional padding techniques to 65 Dacron/35 cotton poplin to achieve a 2 per cent dry siloxane loading. The padding bath contained 19 parts of the emulsion, 179 parts of water, and 2 parts of a zinc/tin soap emulsion as the catalyst. The fabric was then cured at 150°C. for 5 minutes. The dried treated fabrics were evaluated for water repellency by the spray rating AATCC Test Method 22-1967 after conditioning for 24 hours at 73°F. and 50 per cent relative humidity. Fabric padded immediately after the bath was prepared had a water repellency rating of 100; fabric padded after the same bath had been standing for 24 hours at room temperature showed a satisfactory rating of 70. The same fabric was treated in a similar manner with a padding bath containing a commercially available siloxane of the formula $WY_{40}W$; this product showed similar water repellency ratings. The fabric treated with the siloxane compositions of this invention had a softer, more pleasing hand than did the fabric treated with the commercial siloxane composition. Further comparisons with $WX_{45-60}Z_{3-9}W$ siloxanes showed that water repellency from a freshly prepared padding bath was not as good as is obtained from either of the above.

EXAMPLE 2

Following the procedure described in Example 1, a siloxane was produced having the average structure $WX_{35.2}Y_{8.8}Z_6W$ by reacting 167.4 parts of $WX_{53}Z_9W$, 31.6 parts of $WY_{40}W$ and 1.05 parts of $WW$. The siloxane had a kinematic viscosity of 162 cstks. at 25°C. a Y:X ratio 0.25:1, a Z:X ratio of 0.17:1 and a Y:Z ratio of 1.46:1.

Aqueous emulsions were prepared and used to treat the fabric in the same manner. The Dacron/cotton poplin treated immediately after the padding bath was prepared had a water repellency rating of 100. Dacron taffeta with a 1 per cent dry siloxane loading had a water repellency rating of 90 as compared to an 80–90 rating for a commercially available siloxane composition.

EXAMPLE 3

Following the procedure described in Example 1, a siloxane was produced having the average structure $WX_{28.8}Y_{4.32}Z_{4.89}W$ by reacting 176 parts of $WX_{53}Z_9W$, 20 parts of $WY_{40}W$ and 4 parts of $WW$. The siloxane had a kinematic viscosity of 94 cstks. at 25°C. a Y:X ratio of 0.15:1, a Z:X ratio of 0.17:1 and a Y:Z ratio of 0.89:1.

Aqueous emulsions were prepared and used to treat the fabric in the same manner described in Example 1. The fabric treated immediately after the padding bath was prepared had a water repellency rating of 100.

EXAMPLE 4

Following the procedure described in Example 1 but using 2.6 parts of 93 per cent sulfuric acid as catalyst and stirring at 25°C. for 6 hours a siloxane was produced having the average structure $WX_{38}Y_{8.8}Z_{5.5}W$ by reacting 32 parts of $WX_{48}Z_{12}W$, 61 parts $WX_{53}Z_9W$, 20 parts of $WY_{40}W$, 15 parts of the $X_4$ cyclic siloxane and 3 parts of $WW$. The mixture was decanted to remove the bulk of the catalyst and then neutralized with sodium bicarbonate, stipped to remove lites and filtered. The siloxane had a kinematic viscosity of 63 cstks. at 25°C., a Y:X ratio of 0.23:1, a Z:X ratio of 0.14:1 and a Y:Z Z ratio of 1.6:1.

Aqueous emulsions were prepared and evaluated as described in Example 1 on 65 Dacron/35 cotton poplin and on 80 × 80 cotton fabrics at a one per cent dry siloxane loading. Both fabrics had an initial water repellency rating of 100. After 5 washes in accord with AATCC Test Method 124-1969 the cotton had a rating of 50 to 70. In comparison, the commercially available $WY_{40}W$ siloxane showed an initial rating on cotton of 100 but a rating of 0 after 5 washes. It was found that the siloxane of this Example 4 showed superior and unexpected and unobvious advantages over the $WY_{40}W$ siloxane in its water repellency properties in that water repellency was retained at lower loadings thereof. This is shown in the following table wherein the water repellency ratings of each siloxane at varying loadings are set forth for the cotton fabric.

|  | Example 4 | $WY_{40}W$ |
| --- | --- | --- |
| 0.2 | 70 | 50 |
| 0.4 | 90 | 70 |
| 0.6 | 90 | 80 |
| 0.8 | 100 | 90 |
| 1.0 | 100 | 100 |
| 1.2 | 100 | 100 |

Thus, it can be seen that lower loadings can be used to achieve the same results achieved by present commercial materials.

EXAMPLE 5

A mixture of 22 parts of trimethylchlorosilane, 412 parts of dimethyldichlorosilane and 56 parts of dichlorosilane was gradually added to a mixture of 128 parts of 35 per cent hydrochloric acid and reacted at 0° to 10°C. for 8 hours. The layers were separated by decantation and the siloxane prepolymer layer dried over concentrated sulfuric acid. This prepolymer was added to 54 parts of $WY_{40}W$ and 6 parts of concentrated sulfuric acid as catalyst. The mixture was stirred at room temperature for 9 hours. The catalyst was removed by decantation and the residual siloxane neutralized with sodium bicarbonate, stripped to remove lites and filtered. The siloxane had a kinematic viscosity of 78 cstks. at 25°C., a Y:X ratio of 0.25:1, a Z:X ratio of 0.17:1 and a Y:Z ratio of 1.4:1. The average structural formula was $WX_{49}Y_{12}Z_{8.3}W$.

Aqueous emulsions were prepared and evaluated as described in Example 4, except that zinc stearate was padding sole catalyst added to the padding bath. When evaluated on 80 × 80 cotton this siloxane showed water repellency ratings of 100 at loading of one per cent down to 0.2 per cent. In comparison, the $WY_{40}W$ siloxane showed ratings of 100 at loadings of 0.8 per cent or higher, ratings of 90 at loadings of 0.4 per cent or higher and a rating of 80 at loadings of 0.2 per cent.

We claim:

1. An article of manufacture, a textile having improved water repellency, said textile having been treated with about 0.2 to about 3 weight per cent, based on the dry weight of the textile, of a quadripolymer siloxane having the average structure

in which a has a value of from 27 to 55, b has a value of from 4 to 15, c has a value of 4.5 to 10, the ratio of b:a is from 0:1:1 to 0.35:1, the ratio of c:a is from 0.1:1 to 0.25:1, the ratio of b:c is from 0.9:1 to 1.6:1, the degree of polymerization is from about 35 to 80; and R is alkyl of from 1 to 3 carbon atoms.

2. The article of claim 1 wherein the ratio of b:a is 0.15:1, the ratio of c:a is 0.17:1, 1, and the ratio of b:c is from 1.5:1 to 1.6:1 in said quadripolymer.

3. The article of claim 1 wherein the degree of polymerization in said quadripolymer is from 38 to 55.

4. The article of claim 2 wherein the degree of polymerization in said quadripolymer is from 38 to 55.

5. An article of manufacture, a paper having improved water repellency and release properties, said paper having been treated with about 0.2 to about 3 weight per cent, based on the dry weight of the textile, of a quadripolymer siloxane having the average structure

in which a has a value of from 27 to 55, b has a value of from 4 to 15, c has a value of 4.5 to 10, the ratio of b:a is from 0.1:1 to 0.35:1, the ratio of c:a is from 0.1:1 to 0.25:1, the ratio of b:c is from 0.9:1 to 1.6:1, the degree of polymerization is from about 35 to 80; and R is alkyl of from 1 to 3 carbon atoms.

* * * * *

UNITED STATES PATENT OFFICE
CERTIFICATE OF CORRECTION

Patent No. 3,967,030          Dated June 29, 1976

Inventor(s) G.C. Johnson, R.B. Metzler, D. L. Bailey

It is certified that error appears in the above-identified patent and that said Letters Patent are hereby corrected as shown below:

The formulas on column 1, lines 28 to 36 should be read as:

$$W = R\underset{R}{\overset{R}{Si}}O_{1/2}- \qquad X = -\underset{R}{\overset{R}{Si}}O-$$

$$Y = -\underset{H}{\overset{R}{Si}}O- \qquad Z = -\underset{H}{\overset{H}{Si}}O-$$

Column 1, line 47, the term "0.17:1;1;" should read ---0.17:1;---.

Column 4, line 38, the term "Y:ZZ" should read ---Y:Z---.

Column 6, line 13, the term "0.17:1, 1," should read ---0.17:1,---

Signed and Sealed this

Nineteenth Day of October 1976

[SEAL]

Attest:

RUTH C. MASON
Attesting Officer

C. MARSHALL DANN
Commissioner of Patents and Trademarks